United States Patent [19]
Devlin et al.

[11] Patent Number: 5,300,043
[45] Date of Patent: Apr. 5, 1994

[54] SUCTION CATHETER VALVE

[75] Inventors: Thomas Devlin, Cambridge; Victor Cheung, Arlington; Karl Ulrich, Belmont, all of Mass.

[73] Assignee: Smiths Industries Medical Systems, Inc., Keene, N.H.

[21] Appl. No.: 965,998

[22] Filed: Oct. 23, 1992

[51] Int. Cl.$^5$ .............................................. A61M 5/00
[52] U.S. Cl. ..................................... 604/250; 604/902
[58] Field of Search ................. 604/33, 34, 119, 246, 604/171, 163, 249, 250, 902; 128/207.16, 912

[56] References Cited

U.S. PATENT DOCUMENTS

| | | |
|---|---|---|
| 194,664 | 8/1877 | Farley . |
| 2,471,623 | 5/1949 | Hubell . |
| 3,262,670 | 7/1966 | Marlett . |
| 3,438,607 | 4/1969 | Williams et al. ................. 604/34 |
| 3,497,175 | 2/1970 | Koland . |
| 3,628,532 | 12/1971 | Magrath . |
| 3,911,919 | 10/1975 | Raitto . |
| 4,015,336 | 4/1977 | Johnson . |
| 4,036,210 | 7/1977 | Campbell et al. . |
| 4,047,527 | 9/1977 | Kelsen . |
| 4,193,406 | 3/1980 | Jinotti . |
| 4,212,300 | 7/1980 | Meals . |
| 4,300,550 | 11/1981 | Gandi et al. . |
| 4,328,946 | 5/1982 | Morin . |
| 4,356,823 | 11/1982 | Jackson . |
| 4,414,999 | 11/1983 | Basta . |
| 4,552,142 | 11/1985 | Hoffman et al. . |
| 4,559,045 | 12/1985 | Danby et al. . |
| 4,569,344 | 2/1986 | Palmer . |
| 4,573,965 | 3/1986 | Russo . |
| 4,617,013 | 10/1986 | Betz ..................................... 604/902 |
| 4,638,539 | 1/1987 | Palmer . |
| 4,662,871 | 5/1987 | Rafelson . |
| 4,691,702 | 9/1987 | Chantzis . |
| 4,696,296 | 9/1987 | Palmer . |
| 4,731,052 | 3/1988 | Seitz, Jr. ............................. 604/34 |
| 4,759,349 | 7/1988 | Betz et al. .......................... 604/902 |
| 4,805,611 | 2/1989 | Hodgkins . |
| 4,836,199 | 6/1989 | Palmer . |
| 4,850,350 | 7/1989 | Jackson . |
| 4,872,579 | 10/1989 | Palmer . |
| 5,000,175 | 3/1991 | Pue . |
| 5,083,561 | 1/1992 | Russo . |
| 5,139,018 | 8/1992 | Brodsky et al. . |
| 5,147,292 | 9/1992 | Kullas et al. ....................... 604/34 |
| 5,230,704 | 7/1993 | Moberg et al. ..................... 604/34 |

FOREIGN PATENT DOCUMENTS 0150666  8/1985  European Pat. Off. ............ 604/250

*Primary Examiner*—John D. Yasko
*Assistant Examiner*—Anthony Gutowski
*Attorney, Agent, or Firm*—Pollock, Vande Sande & Priddy

[57] ABSTRACT

A closed system suction catheter assembly has a valve which controls suction applied at the patient end of the assembly. The valve has a pinch tube connected in line with the catheter and secured at each end to the housing of the valve. An occluder bar midway along a pivoted lever is urged up by a spring to pinch the tube closed against a fixed occluder and close the valve. The valve has a button protected by a rotatable guard which bears on an end of the lever so that the valve can be opened by pressing down on the button. A snap mechanism engages the occluder lever.

8 Claims, 4 Drawing Sheets

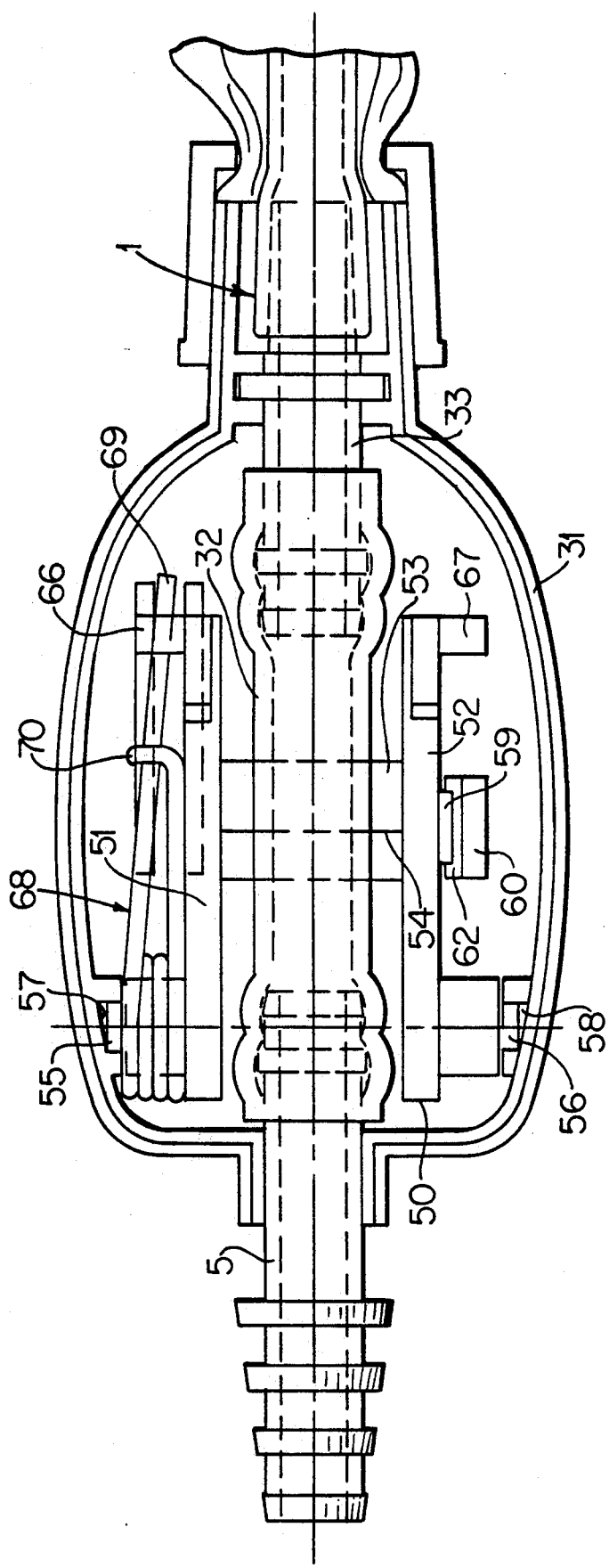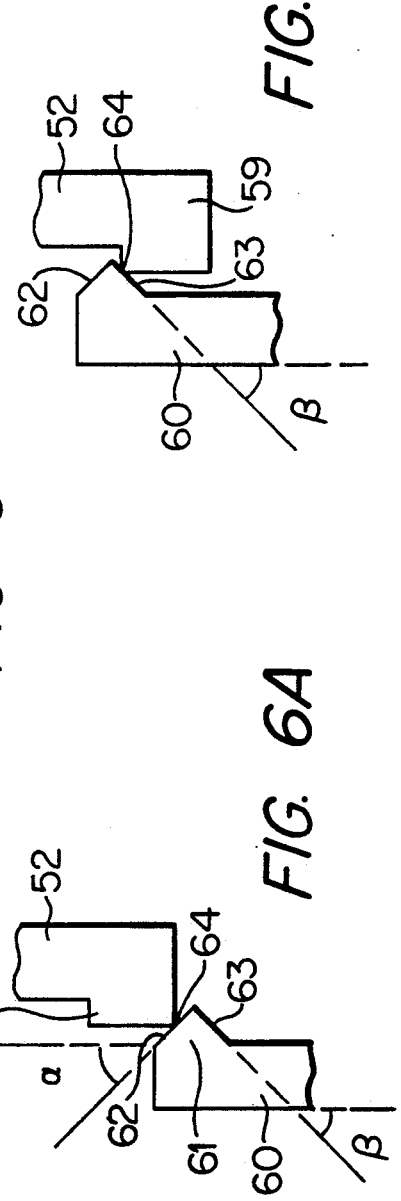

SUCTION CATHETER VALVE

BACKGROUND OF THE INVENTION

This invention relates to suction catheter assemblies and valves.

The invention is more particularly concerned with medical suction catheter assemblies including valves which can be used for aspirating secretions from tracheal tubes or, for example, for removing blood and debris from surgical sites.

Suction catheter assemblies of this kind are connected to the inlet of a container, the outlet of the container being connected to a vacuum pump so that a reduced pressure is created in the container which in turn applies suction to the catheter. In such systems, the vacuum pump generally operates continuously and the catheter includes a valve by which suction at the tip of the catheter can be controlled. In its simplest form, the valve comprises an aperture in the wall of the catheter which, when open, allows air to enter the catheter and thereby prevents any significant suction effect at the tip. The aperture can be closed, when desired, by the thumb of the user, or by a movable flap, so that the suction effect is confined to the tip of the catheter.

Examples of such catheters are described in U.S. Pat. No. 3,911,919 and U.S. Pat. No. 4,468,216. The problem with this form of valve is that the suction control aperture provides a path through which contaminated material sucked into the catheter can leak out. This is a significant disadvantage in view of the present concern about cross-infection and the transmission of infectious diseases.

In order to reduce the risk of escape of material, catheters have been made which include a sealed valve. Examples of suction catheters with a push-down spool valve are shown in U.S. Pat. No. 4,680,026, U.S. Pat. No. 4,526,573 and U.S. Pat. No. 4,502,508. A suction catheter with a resilient valve member is described in U.S. Pat. No. 4,569,344. Many other forms of suction catheter with different suction control valves are also known.

One problem with these valves is that they have as a part of their sealing system an obstruction to flow. The obstruction is created by the stem which connects the spool, plunger or other seal to the manually-actuable button by which the valve is operated. In some valves the stem itself creates the seal. The obstruction created by the stem causes the fluid flow path to be split into two paths around opposite sides of the stem. This does not permit the free flow of thick fluids, such as thick respiratory fluids.

BRIEF SUMMARY OF THE PRESENT INVENTION

It is an object of the present invention to provide systems that can be used to alleviate the above-mentioned problems.

According to one aspect of the present invention there is provided a suction catheter assembly comprising a suction catheter and a valve connected to the catheter to control flow of fluid along the catheter, the valve comprising: a housing, a length of resilient tube, means coupling the tube with the catheter, means securing the tube with the housing at two spaced locations, first and second occluder members located directly opposite one another on opposite sides of the resilient tube between the spaced locations, resilient means that urges at least the first occluder member towards the second occluder member so that the resilient tube is squeezed closed between the two occluder members, and manually-engageable means coupled with said first occluder member such that by engaging the manually-engageable means, the first occluder member can be displaced away from the second occluder member and the resilient tube allowed to open to permit fluid flow through the catheter.

The first occluder member is preferably in the form of a lever, the lever having a pivot close to one end, means coupling the lever close to its other end to the manually-engageable means, and engagement means between its ends which engages the resilient tube. The second occluder member may include a plate against which the resilient tube is squeezed closed by the first occluder member. The plate may be fixed with the housing. The assembly preferably includes a snap-action member that engages the first occluder member and gives the first occluder member a snap action on opening and closing the valve. The snap-action member may include an upper inclined surface and a lower inclined surface, the first occluder member including a detent and the detent being arranged to engage one of the inclined surfaces when the first occluder member is displaced away from the second occluder member and to engage the other of the inclined surfaces when the first occluder member is displaced towards the second occluder member. The manually-engageable means is preferably a button that is pushed down to open the valve and permit suction. The assembly may include a guard extending a part way around the manually-engageable means to prevent inadvertent actuation of the valve. Preferably, the guard is rotatable relative to the housing.

According to another aspect of the present invention there is provided a suction catheter assembly comprising: a suction catheter; a patient coupling located towards one end of the assembly, the patient coupling including a sliding seal through which the catheter can be advanced into the patient; a protective sleeve extending along the catheter from the patient coupling; and a valve comprising: a housing, a length of resilient tube, means coupling the tube with the catheter, means securing the tube with the housing at two spaced locations, first and second occluder members located directly opposite one another on opposite sides of the resilient tube between the spaced locations, resilient means that urges at least the first occluder member towards the second occluder member so that the resilient tube is squeezed closed between the two occluder members, and manually-engageable means coupled with said first occluder member such that by engaging the manually-engageable means, the first occluder member can be displaced away from the second occluder member and the resilient tube allowed to open to permit fluid flow through the catheter.

A suction catheter assembly according to the present invention, will now be described, by way of example, with reference to the accompanying drawings.

BRIEF DESCRIPTION OF THE DRAWINGS

FIG. 5 is a cut-away plan view of the valve; and

FIGS. 6A and 6B illustrate operation of the valve.

DESCRIPTION OF THE PREFERRED EMBODIMENTS

Figure 1:
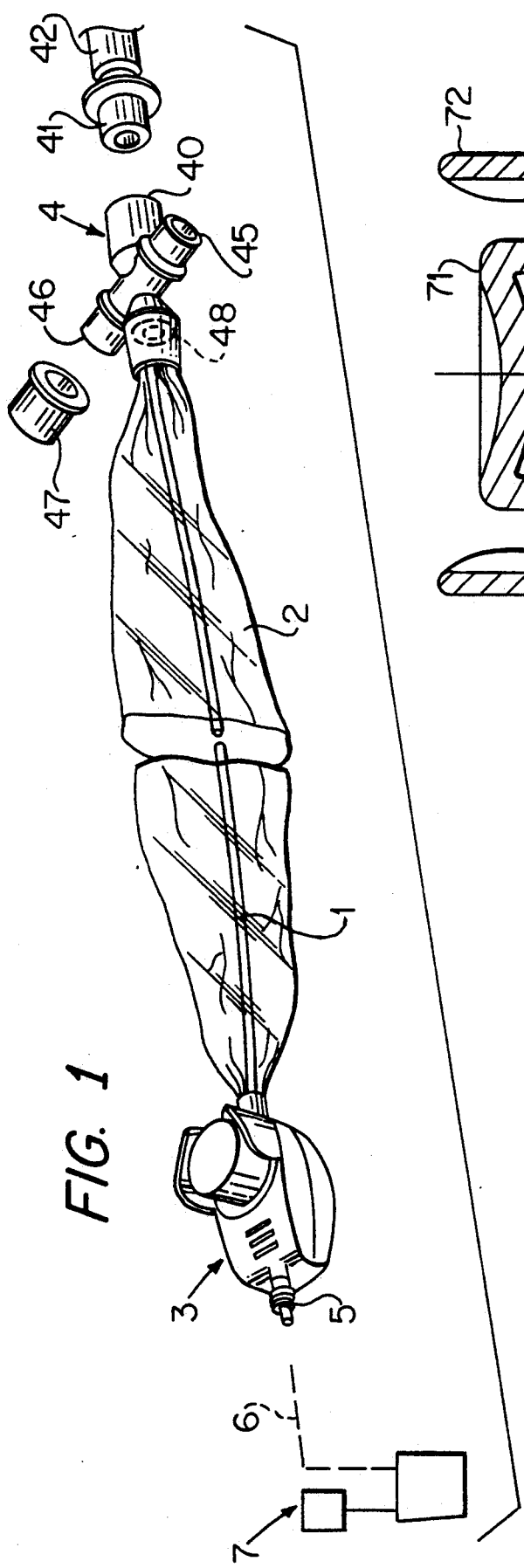
FIG. 1 is a perspective view of the assembly.

With reference first to FIG. 1, the suction catheter assembly comprises an aspirating catheter 1 that extends within a flexible, protective sleeve 2 between a valve assembly 3 and a patient connecting member 4.

The aspirating catheter 1 is of conventional construction having an outside diameter of about 4–5 mm and a length of about 55 cm. At its machine or proximal end, the catheter 1 is secured to the valve assembly 3.

The valve assembly 3 has a fluid passageway extending along it which communicates at one end with the catheter 1 and at the other end with a spigot 5. In use, the spigot 5 is connected to tubing 6 which extends to a suction source 7. The valve 3 normally prevents flow through the catheter 1 but can be manually actuated by the user to open and connect the lumen of the catheter to the suction source 7.

The patient connecting member 4 is of generally cruciform shape. At its distal, or patient end, the connecting member 4 has a female luer coupling 40 which is aligned with the axis of the member. The coupling 40 is adapted to be connected to a cooperating coupling 41 on the end of a tracheal tube 42. Two sides ports 45 and 46 extend at right angles to the axis of the connecting member, directly opposite one another, about midway along the length of the connecting member. These two side ports 45 and 46 communicate directly with the interior of the coupling 40 and are used in the conventional manner to connect with ventilation apparatus. One port may be used for inhalation gas and the other port used for exhalation gas. Alternatively, one of the ports 46 may be closed by a cap 47 and inhalation and exhalation both be effected through the other port 45.

The patient connecting member 4 also includes a sliding seal 50 in the form of a resilient disc or diaphragm with a central aperture through which the catheter 1 extends as a sliding fit.

With reference now also to FIGS. 2 to 6, the valve assembly 3 has a housing with an upper and lower part 30 and 31 joined together around their edges. A resilient rubber pinch tube 32 is secured at its proximal end onto the internal end of the spigot 5 which extends into the proximal, left-hand end of the assembly. At its distal end, the tube 32 is secured onto the end of a second spigot 33 which projects out of the right-hand end of the assembly.

The valve 3 also includes an occluder lever 50 which extends within the valve housing 30, 31 below the pinch tube 32. The occluder lever 50 comprises two side arms 51 and 52 linked together approximately midway along their length by a lateral bar 53. The bar 53 is of triangular section with an occluding edge 54 on its upper surface. Because the occluding edge 54 is located about half way along the lever 50, the lever has a mechanical advantage of about 2:1. This enables the lever 50 to exert a relatively high closing force on the tube 32 whilst enabling the lever to be pushed down relatively easily at its end.

Figure 4:
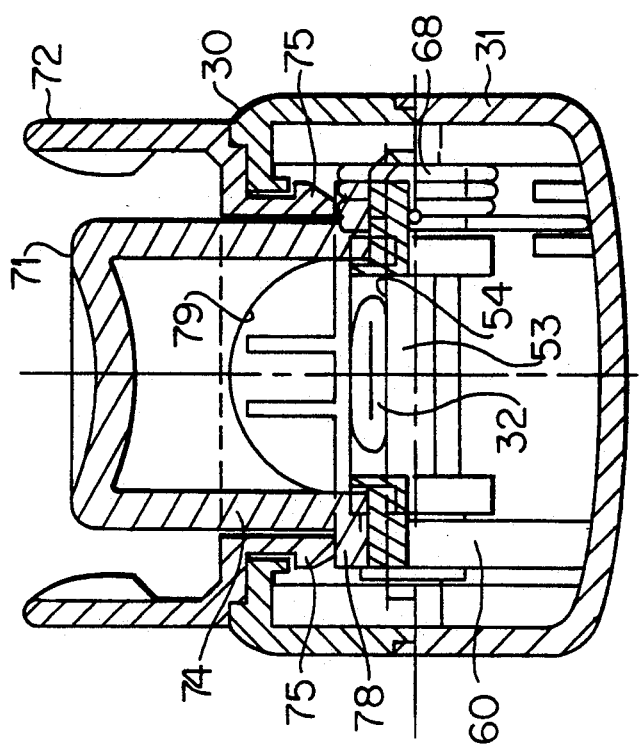
FIG. 4 is a transverse sectional elevation of the valve along the line IV—IV of FIG. 3.
Figure 2:
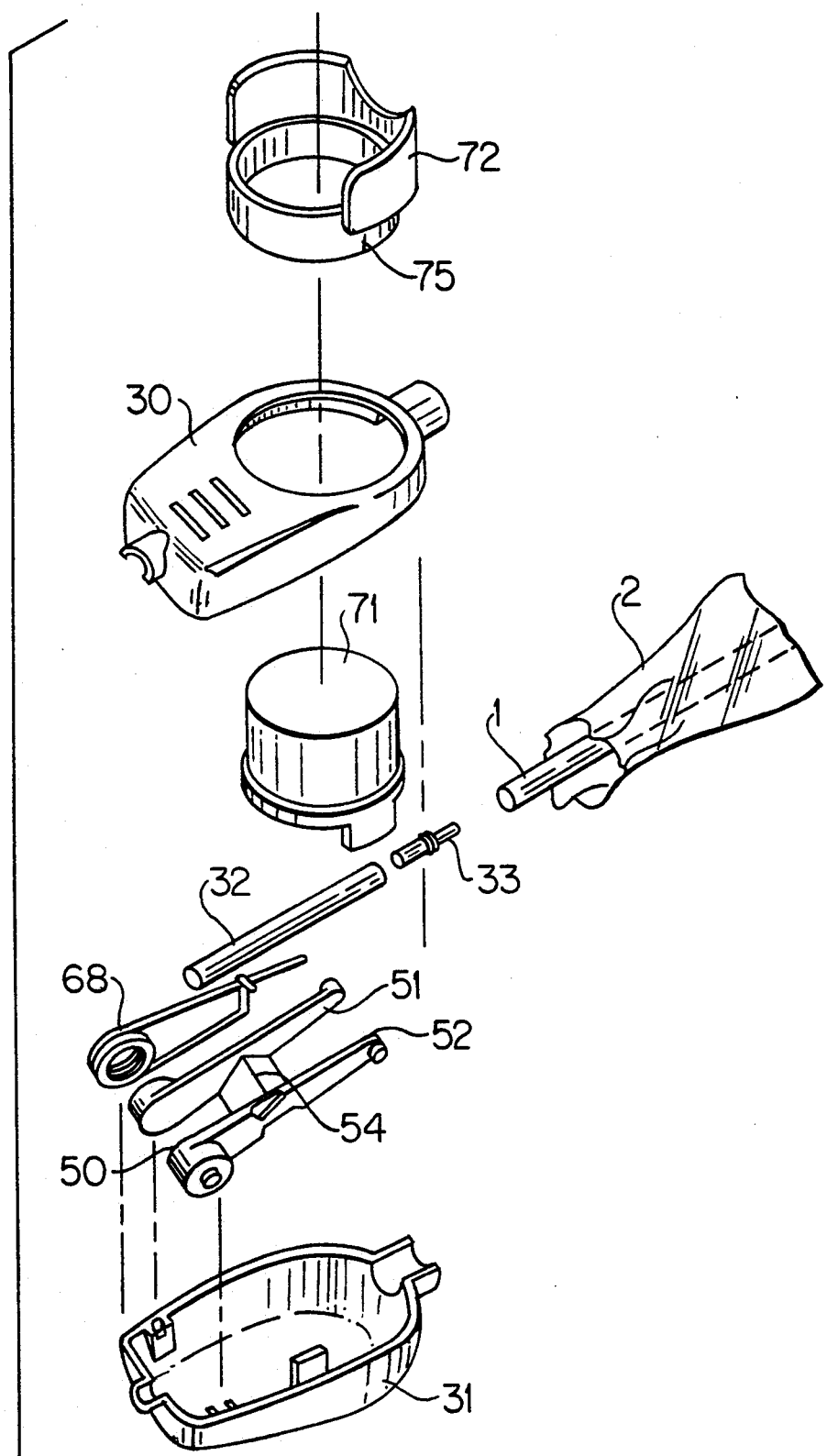
FIG. 2 is a simplified exploded view of a valve of the assembly.
Figure 3:
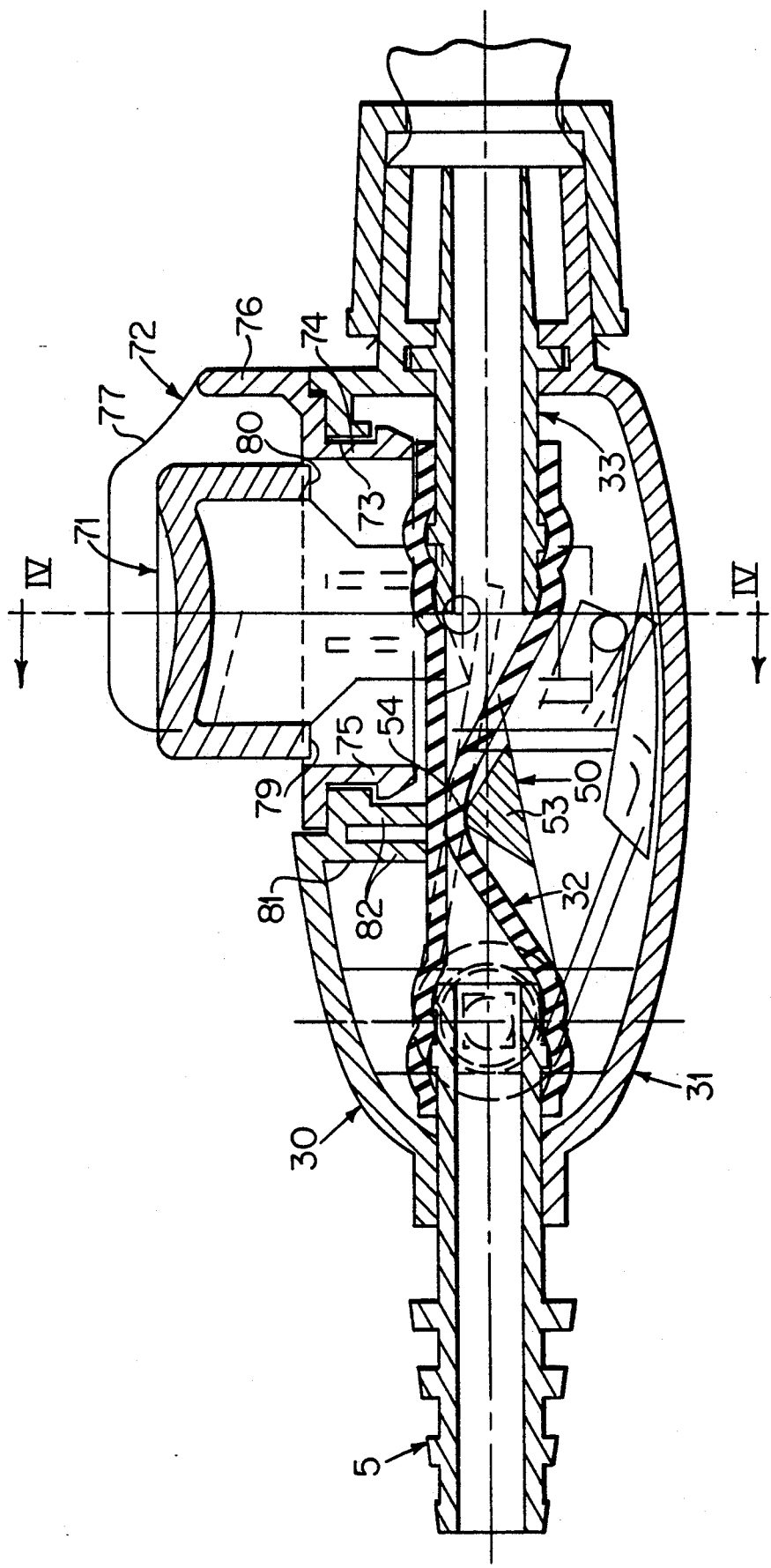
FIG. 3 is a sectional side elevation of the valve.

At their proximal end, the side arms 51 and 52 both have outwardly-projecting bearing studs 55 and 56 which are located in bearing recesses 57 and 58 formed in the lower housing 31. One of the side arms 52 is formed with a detent 59, in the region of the lateral bar 53, which cooperates with a snap arm 60 that projects upwardly from the floor of the lower housing 31. At the upper end of the snap arm 60 there is a triangular catch 61 that projects towards the occluder lever 50 and engages the detent 59. The catch 61 has an upper surface 62 that inclines from the vertical by an angle $\alpha$; the catch also has a lower surface 63 that inclines from the vertical by an angle $\beta$. The detent 59 has a lower edge 64 that engages the upper surface 62 of the catch 61 (FIG. 6A) and an upper edge 65 that engages the lower surface 63 of the catch (FIG. 6B) depending on whether the occluder lever 50 is in its upper position A (as shown in FIGS. 3 and 4) or its lower position B. Thus, when the occluder lever 50 is displaced down, the detent 59 slides over the upper surface 62 of the catch; and, when the lever is displaced up, the detent slides over the lower surface 63 of the catch.

At the distal end of the occluder lever 50, the side arms 51 and 52 have outwardly projecting fingers 66 and 67. A torsion spring 68 extends within the valve housing 30, 31 alongside the occluder lever 50. The spring 68 is formed by a resilient wire which is wound into several turns about the bearing stud 55 and has two ends 69 and 70 that are urged apart. One end 69 of the spring 68 extends beneath the finger 66 on the occluder lever 50 whereas the other end 70 is bent into a hook above the first end so as to limit upwards displacement of the first end. In this way, the spring 68 urges the occluder lever 50 upwardly at the distal end.

The valve 3 also includes a manually-operable button 71 and a guard 72 which project through a circular aperture 73 in the upper housing 30. The guard 72 comprises a lower ring 74, the external diameter of which is equal to the diameter of the aperture 73, which has four radially-projecting tapered lugs 75 spaced around the ring. The lower end of the lugs 75 are inclined so that the guard can be pushed down into the aperture 73 until the lugs snap under the edge of the aperture and prevent subsequent removal of the guard. A part-cylindrical wall 76 extends around the outside of the ring 74 overlapping the aperture 73 in the upper housing 30. A semicircular notch 77 is formed in the top edge of the wall 76 midway along its length to prevent the guard catching on long fingernails. The height of the wall 76 is slightly greater than to the distance by which the button 71 projects above the upper housing 30. The guard 72 can be rotated in the aperture 73 to allow access to the button 71 from different positions. The button 71 is of cylindrical shape and projects through the aperture 73 and the ring 74 of the guard 72. Toward its lower end, the button 71 has an annular shoulder 78 which is larger than the internal diameter of the ring 74 and thereby limits the extent of upward displacement of the button. The shoulder 78 rests on the fingers 66 and 67 on the occluder lever 50, the button being formed with two, opposite semi-circular recesses 79 and 80 at its lower end to provide clearance for the pinch tube 32 when the button is depressed.

A fixed occluder 81 projects down from the roof of the upper housing 30, the occluder being provided by two, closely spaced vertical plates 82. The occluder 81 is located above the pinch tube 32 in line with the bar 53 of the occluder lever 50. The location of the occluder 81 is such that, in the valve's natural state, the spring 68 urges the occluder lever 50 and the button 71 upwardly so that the bar 53 of the occluder contacts the pinch tube 32 and deforms it upwardly against the occluder 81 thereby pinching the tube and closing the valve. It can be seen, therefore, that flow of fluid along the assembly is prevented by contact of opposite sides of the internal surface of the pinch tube with each other. The wall of pinch tube itself is uninterrupted and provides no site for leakage. Because there is no need for there to be any seal in the valve between the button 71 and the housing 30, 31 or between the occluders 50, 81 and the pinch tube 32, the construction of the valve is simplified without any risk of leakage and contamination.

In operation, the coupling 40 of the patient connecting member 4 is secured to the coupling 41 on the end of the tracheal tube 42 and its side ports 45 and 46 are connected to a ventilator. The valve 3 is connected to the suction source 7 but, as long as the valve 3 remains unactuated, no suction is applied to the catheter 1.

When aspiration of fluid from the trachea or bronchi is required, the user grips the catheter 1 through the sleeve 2 and pushes it forwardly so that the distal, patient end of the catheter is advanced through the connecting member 4 and the sliding seal 50 and into the tracheal tube 42. When the catheter 1 has been inserted to the desired depth, the user depresses the button 71 on the valve 3 so that the catheter is connected to the suction source 7 and fluid in the vicinity of the tip of the catheter is sucked into the catheter and removed. The snap-action mechanism of the lever 50 gives the button 71 also a snap action so that it has a positive feel. It also ensures that the valve is either fully open or fully closed which has the advantage of avoiding undesirable partial suctioning. During aspiration, ventilation of the patient occurs normally. When aspiration is complete, the catheter 1 is pulled back into the sleeve 2, the assembly remaining attached to the tracheal tube connector 41 so that it can be reused when necessary.

Because the natural state of the valve 3 is closed, with the tube 32 pinched close, prolonged storage may cause opposite sides of wall of the tube to stick together where they contact. To avoid this, the valve may be held open during storage. For example, a clip may be fastened between the top of the button 71 and the lower surface of the housing 31 to keep the button depressed. Alternatively, a rod could be inserted through the spigot 5 into the pinch tube 32 while the button was held down so that, during storage, the rod maintains the pinch tube in a circular shape. The rod would be removed before use.

What we claim is:

1. A suction catheter assembly comprising a suction catheter and a valve connected to the catheter to control flow of fluid along the catheter, the valve comprising: a housing, a length of resilient tube, means coupling the tube with the catheter, means securing the tube length of resilient tube, means coupling the tube with the catheter, means securing the tube with the housing at two spaced locations, first and second occluder members located directly opposite one another on opposite sides of the resilient tube between the spaced locations, resilient means that urges at least the first occluder member towards the second occluder member so that the resilient tube is squeezed closed between the two occluder members, and manually-engageable means coupled with said first occluder member such that by engaging the manually-engageable means, the first occluder member can be displaced away from the second occluder member and the resilient tube is allowed to open to permit fluid flow through the catheter, wherein the first occluder member is in the form of a lever, and wherein the lever has a pivot close to one end, means coupling the lever close to its other end to the manually-engageable means, and engagement means between its ends which engages the resilient tube.

2. A suction catheter assembly according to claim 1, wherein the second occluder member includes a plurality of closely-spaced plates having a lower end against which the resilient tube is squeezed closed by the first occluder member.

3. A suction catheter assembly according to claim 1, wherein the second occluder member is fixed with the housing.

4. A suction catheter assembly according to claim 1, including a snap-action member, and wherein the snap-action member engages the first occluder member and gives the first occluder member a snap action on opening and closing the valve.

5. A suction catheter assembly according to claim 1, wherein the said manually-engageable means is a button that is pushed down to open the valve and permit suction.

6. A suction catheter assembly according to claim 1, including a guard, said guard extending a part way around the manually-engageable means to prevent inadvertent actuation of the valve.

7. A suction catheter assembly comprising a suction catheter and a valve connected to the catheter to control flow of fluid along the catheter, the valve comprising:
   a housing;
   a length of resilient tube;
   means coupling the tube with the catheter;
   means securing the tube with the housing at two spaced locations;
   first and second occluder members located directly opposite one another on opposite sides of the resilient tube between the spaced locations;
   resilient means for urging at least the first occluder member towards the second occluder member so that the resilient tube is squeezed closed between the two occluder members;
   a snap-action member having an upper inclined surface and lower inclined surface;
   manually-engageable means coupled with said first occluder member, said first occluder member including a detent, arranged to engage one of the inclined surfaces when the manually-engageable means is engaged and the first occluder member is displaced away from the second occluder member to allow the resilient tube to open and permit fluid flow through the catheter, the detent being arranged to engage the other of the inclined surfaces when the first occluder member is displaced towards the second occluder member.

8. A suction catheter assembly comprising a suction catheter and a valve connected to the catheter to control flow of fluid along the catheter, the valve comprising:
   a housing, a length of resilient tube, means coupling the tube with the catheter, means securing the tube with the housing at two spaced locations, first and second occluder members located directly opposite one another on opposite sides of the resilient tube between the spaced locations, resilient means that urges at least the first occluder member towards the second occluder member so that the resilient tube is squeezed closed between the two occluder members, manually-engageable means coupled with said first occluder member such that by engaging the manually-engageable means, the first occluder member can be displaced away from the second occluder member and the resilient tube is allowed to open to permit fluid flow through the catheter, and a guard, said guard being rotatable and extending a part way around the manually-engageable means to prevent inadvertent actuation of the valve.

* * * * *